United States Patent
Weber et al.

(10) Patent No.: US 9,671,380 B2
(45) Date of Patent: Jun. 6, 2017

(54) METHOD FOR DIAGNOSING PARTICULATE MATTER SENSOR DETERIORATION

(71) Applicant: DELPHI TECHNOLOGIES, INC., Troy, MI (US)

(72) Inventors: Konrad A. Weber, Rehlingen-Siersburg (DE); David A. Goulette, Marine City, MI (US)

(73) Assignee: DELPHI TECHNOLOGIES, INC., Troy, MI (US)

( * ) Notice: Subject to any disclaimer, the term of this patent is extended or adjusted under 35 U.S.C. 154(b) by 296 days.

(21) Appl. No.: 14/504,478

(22) Filed: Oct. 2, 2014

(65) Prior Publication Data

US 2016/0097752 A1    Apr. 7, 2016

(51) Int. Cl.
*G01N 33/00* (2006.01)
*G01M 15/10* (2006.01)
*G01K 13/00* (2006.01)
*G01K 7/16* (2006.01)

(52) U.S. Cl.
CPC ........... *G01N 33/0006* (2013.01); *G01K 7/16* (2013.01); *G01K 13/00* (2013.01); *G01M 15/102* (2013.01); *G01N 33/0073* (2013.01)

(58) Field of Classification Search
CPC ........... G01M 15/102; G01N 33/0006; G01N 33/0073; G01N 27/4163; G01N 27/4175; F02D 41/222; F02D 41/1466
USPC ................................. 73/1.06, 1.02
See application file for complete search history.

(56) References Cited

U.S. PATENT DOCUMENTS

| | | |
|---|---|---|
| 7,954,230 B2 | 6/2011 | Nelson |
| 2008/0282769 A1 | 11/2008 | Nelson |
| 2008/0283398 A1 | 11/2008 | Nelson et al. |
| 2012/0119759 A1 | 5/2012 | Nelson et al. |
| 2013/0000678 A1 | 1/2013 | Hocken et al. |
| 2015/0168285 A1* | 6/2015 | Hedayat .............. G01M 15/102 73/23.33 |
| 2016/0097704 A1* | 4/2016 | Lin .................... G01N 15/0656 73/1.06 |

* cited by examiner

*Primary Examiner* — Helen Kwok
*Assistant Examiner* — Nashmiya Fayyaz
(74) *Attorney, Agent, or Firm* — Joshua M. Haines

(57) ABSTRACT

A method is presented for diagnosing a particulate matter sensing system, where the system includes a sensing element having two electrodes spaced from one another. The method determining at a first time during a cool-down event a first sensing element temperature and a resistance of the sensing element, and determining at a later second time during the cool-down event a second sensing element temperature and the resistance of the sensing element. The method further includes calculating a predicted sensing element resistance at the second sensing element temperature, based on the first sensing element temperature, the resistance of the sensing element determined at the first time, and a predetermined model of the resistance vs. temperature characteristics of the sensing element. A fault condition for the system may be indicated based on a comparison of the predicted sensing element resistance at the second sensing element temperature and a measured sensing element resistance.

17 Claims, 4 Drawing Sheets

METHOD FOR DIAGNOSING PARTICULATE MATTER SENSOR DETERIORATION

BACKGROUND OF THE INVENTION

Soot sensors, also known as particulate matter (PM) sensors, are often used in vehicles having diesel engines. A particulate matter sensor may be located upstream from a particulate filter, where the sensor is exposed to exhaust flow from the engine having soot particles entrained in the exhaust gas. Alternatively, a particulate matter sensor may be located in a gas stream downstream from a particulate filter, where the sensor is used to monitor the proper operation of the particulate filter.

A known method of sensing soot uses a particulate matter sensor having two electrodes that are spaced from one another and exposed to the gas stream. In the absence of soot, there is very low electrical conductivity (high electrical resistance) between the electrodes. As soot accumulates on the surface of the sensor, soot particles act to bridge the gap between the electrodes. Because the soot particles are electrically conductive the conductivity between the electrodes increases, and this change in conductivity can be related to the amount of soot in the gas stream. Sensors that operate according to this principle are disclosed in US Patent Application Publication 2008/0283398, US Patent Application Publication 2008/0282769, and U.S. Pat. No. 7,954,230, the contents of each of which are hereby incorporated by reference in their entirety.

While the PM sensor is intended to indicate the presence of soot in the exhaust stream, it is possible that a contaminant other than soot may be deposited on the surface of the PM sensor. Such a contaminant may comprise material from additives in fuel or lubricating oil that enter the gas stream to which the sensor is exposed. The presence of such a contaminant on the surface of the particulate matter sensor may interfere with the ability of the sensing electrodes to receive the conductive particulate matter that the sensor is intended to detect, thus preventing the sensor from properly indicating the presence and/or amount of soot in an exhaust stream.

Government regulations require that the particulate matter sensor have self-diagnostics (i.e. On Board Diagnostics or OBD) capability to verify that it is functioning properly. The sensor must be able to verify that the circuit is functioning properly and that if soot lands on the electrode, the sensor can detect it. However, in the presence of contaminants on the sensor, this can be difficult.

Accordingly, the inventors herein have recognized a need for an improved sensing system having a particulate matter sensor that reduces and/or eliminates the foregoing deficiencies.

BRIEF SUMMARY OF THE INVENTION

A method is provided for diagnosing a particulate matter sensing system, wherein the system includes an electronic controller portion, an electrical connection means connected to the controller portion, and a sensing element connected to the electrical connection means. The sensing element includes two electrodes spaced from one another, such that as soot accumulates on the surface of the sensor, soot particles act to bridge the gap between the electrodes. The method includes the steps of determining at a first time during a cool-down event a first sensing element temperature and an resistance of the sensing element, and determining at a second time during the cool-down event a second sensing element temperature and the resistance of the sensing element, the second time occurring later than the first time. The method further includes calculating in the electronic controller portion a predicted sensing element resistance at the second sensing element temperature based on the first sensing element temperature, the resistance of the sensing element determined at the first time, and a predetermined model of the resistance vs. temperature characteristics of the sensing element. In accordance with the method of the invention, the predicted sensing element resistance at the second sensing element temperature is compared to the resistance of the sensing element determined at the second time. A fault condition is indicated if the difference between the predicted sensing element resistance at the second sensing element temperature and the resistance of the sensing element determined at the second time is not within a predetermined range.

BRIEF DESCRIPTION OF THE DRAWINGS

The subject matter which is regarded as the invention is particularly pointed out and distinctly claimed in the claims at the conclusion of the specification. The foregoing and other features, and advantages of the invention are apparent from the following detailed description taken in conjunction with the accompanying drawings in which:

DETAILED DESCRIPTION OF THE INVENTION

As used herein, the term "cool-down event" is used to mean an engine operating regime in which the exhaust temperature is decreasing while the total amount of soot accumulated on the PM sensor is substantially constant. Examples of cool-down events include deceleration fuel cut-off (DFCO) and engine off conditions.

Figure 1:
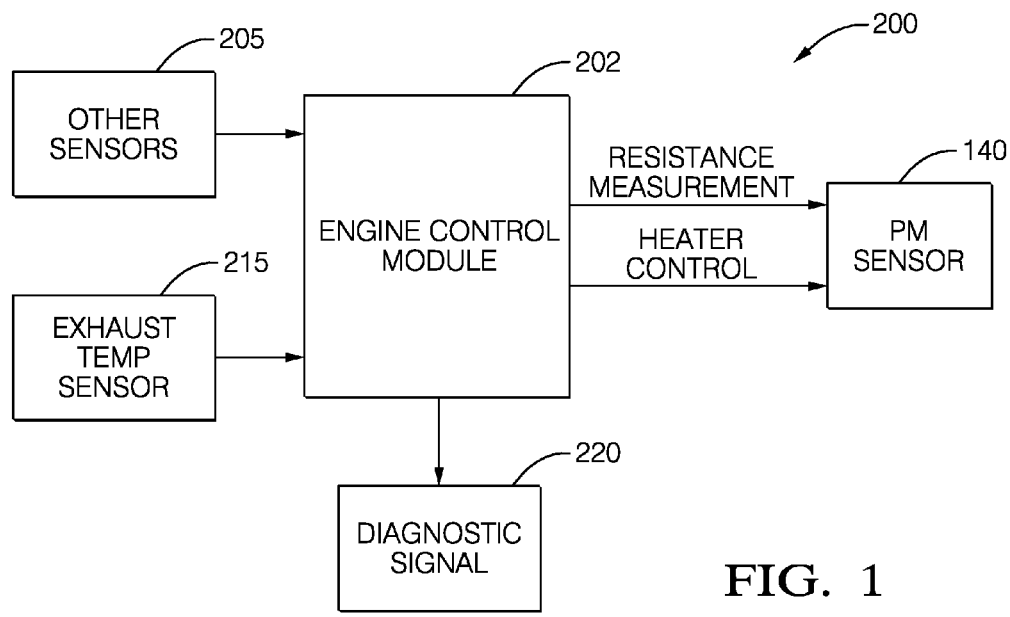
FIG. 1 is a block diagram of a particulate matter sensing system.

Referring now to FIG. 1, a non-limiting example of a particulate sensor diagnostic system 200 is illustrated, which includes a particulate matter sensor 140. The diagnostic system comprises a controller or an engine control module (ECM) 202. Alternatively to an ECM 202, a stand-alone diagnostic module or combined sensor and diagnostic control module may be used. ECM 202 comprises among other elements a microprocessor for receiving signals indicative of the vehicle performance as well as for providing signals for control of various system components, read only memory in the form of an electronic storage medium for executable programs or algorithms and calibration values or constants, random access memory and data buses for allowing the necessary communication (e.g., input, output and within the ECM) with the ECM in accordance with known technologies.

In accordance with an exemplary embodiment the controller 202 will comprise a microcontroller, microprocessor, or other equivalent processing device capable of executing commands of computer readable data or program for executing a control algorithm. In order to perform the prescribed functions and desired processing, as well as the computations therefor (e.g., the control processes prescribed herein, and the like), the controller may include, but not be limited to, a processor(s), computer(s), memory, storage, register(s), timing, interrupt(s), communication interfaces, and input/output signal interfaces, as well as combinations comprising at least one of the foregoing. For example, the controller may include input signal filtering to enable accurate sampling and conversion or acquisitions of such signals from communications interfaces. As described above, exemplary embodiments of the present invention can be implemented through computer-implemented processes and apparatuses for practicing those processes.

The ECM 202 receives various signals from various sensors in order to determine the state of the engine as well as vary the operational state and perform diagnostics. For example, the ECM 202 can determine, based on its input from other sensors 205 and logic and control algorithms whether the engine is being started in a "cold start" state as well as perform and/or control other vehicle operations. Some of the sensors that may be included in the "other sensors" 205 which provide input to the ECM 202 include but are not limited to the following: engine coolant temperature sensor, engine speed sensor, exhaust oxygen sensor, and the like. The sensors used may also be related in part to the type of engine being used (e.g., water cooled, air cooled, diesel, gasoline, hybrid, etc.). The ECM 202 also receives input from exhaust temperature sensor 215, which may be a temperature probe located in the exhaust stream in proximity to the particulate matter sensor or other equivalent means or method for measuring the exhaust temperature.

In accordance with operating programs, algorithms, look up tables and constants resident upon the microcomputer of the ECM various output signals, including control of the heater element 160 (shown in FIG. 3 and FIG. 4) are provided by the ECM 202. The ECM 202 may also provide other control signals to control the engine (e.g., limiting or shutting off fuel flow as well as closing or opening the intake and exhaust valves of the engine) as well as performing other vehicle operations including but not limited to: fuel/air flow control to maintain optimum, lean or rich stoichiometry as may be required to provide the required torque output; spark timing; engine output; and providing on board diagnostic (OBD) means to the vehicle operator.

Figure 2:
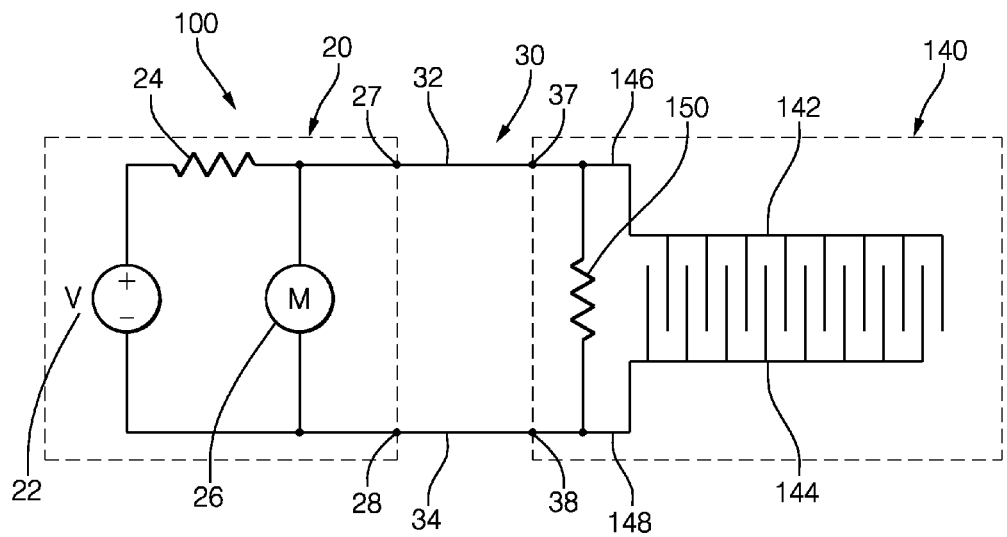
FIG. 2 is an electrical schematic of a portion of a particulate matter sensing system.

FIG. 2 is an electrical schematic of a particulate matter sensing system 100 incorporating a bias resistor, as disclosed in U.S. Patent Application Publication No. 2012/0119759 titled "SELF DIAGNOSTICS OF A PARTICULATE MATTER SENSOR", the contents of which are hereby incorporated by reference in their entirety. The system may be generally considered as partitioned as indicated into a controller portion 20, a wiring harness portion 30, and a sensing element portion 140. The controller portion 20 comprises a means for measuring the resistance of a circuit connected thereto. In the exemplary controller portion 20 in FIG. 1, the resistance measurement means includes a voltage source 22 that provides a voltage value $V_{supply}$, a pull-up resistor 24 having a resistance value $R_{pullup}$, and a voltage measurement means 26. The controller portion 20 electrically interfaces to the wiring harness portion 30 by connection means 27 and 28. The wiring harness portion 30 includes conductors 32 and 34. The wiring harness portion 30 electrically interfaces to the sensing element portion 140 by connection means 37 and 38. The sensing element portion 140 includes a first electrode 142 electrically connected by conductor 146 to connection means 37, and a second electrode 144 electrically connected by conductor 148 to connection means 38. The sensing element portion 140 in FIG. 2 contains an additional bias resistor 150 having a resistance value of $R_{bias}$ electrically connected between conductors 146 and 148.

The resistance of the sensing element $R_{sensor}$ as measured between connection means 37 and connection means 38 is the parallel combination of $R_{bias}$ and the resistance resulting from particulate matter bridging the gap between the first electrode 142 and the second electrode 144. $R_{sensor}$ can be represented mathematically as:

$$R_{sensor} = \frac{R_{bias} \times R_{particulate}}{R_{bias} + R_{particulate}}$$

In the absence of particulate matter on sensing element 140, the term $R_{particulate}$ is very large compared to $R_{bias}$, and the effective sensor resistance $R_{sensor}$ is essentially equal to $R_{bias}$. This condition provides the maximum resistance value of $R_{sensor}$. As particulate matter accumulates so as to bridge the gap between the first electrode 142 and the second electrode 144, the effective sensor resistance $R_{sensor}$ will decrease from its maximum value of $R_{bias}$.

For the particulate matter sensing system 100 depicted in FIG. 2, the voltage measured by measurement means 26 will be:

$$V_{measured} = V_{supply} \frac{R_{sensor}}{R_{pullup} + R_{sensor}}$$

In the absence of particulate matter, the value of $R_{sensor}$ will be at its maximum and will essentially equal $R_{bias}$. Under this condition, the voltage measured by measurement means 26 will be:

$$V_{measured} = V_{supply} \frac{R_{bias}}{R_{pullup} + R_{bias}}$$

Figure 3:
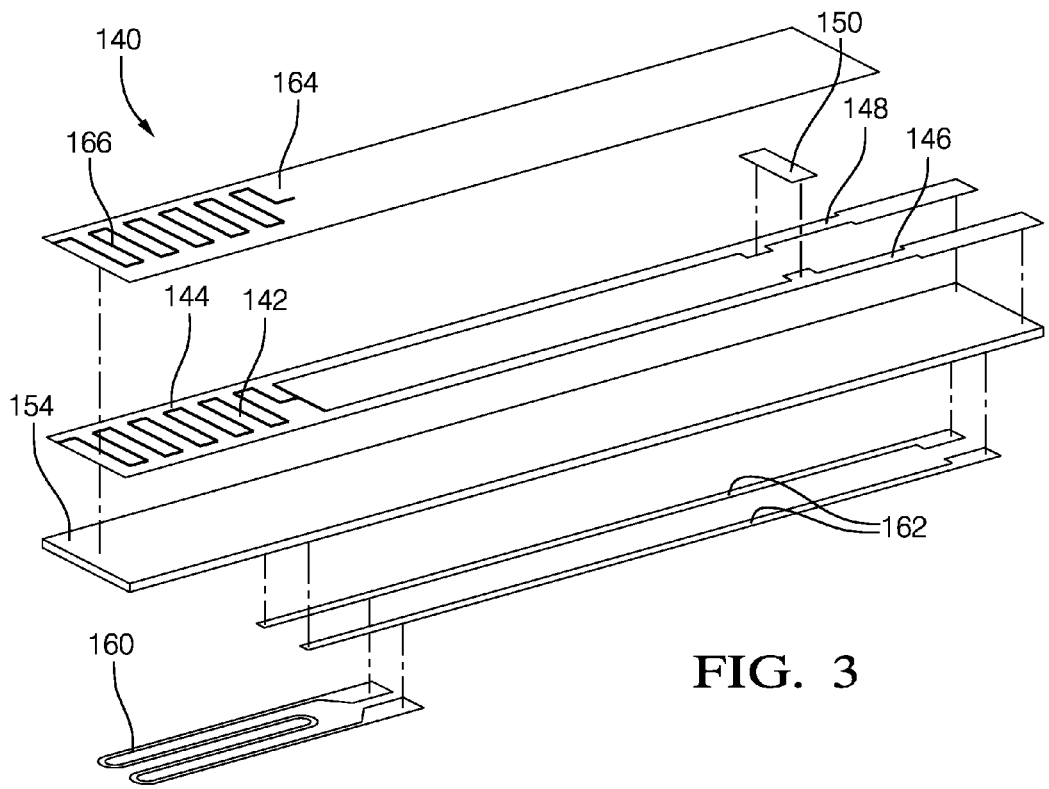
FIG. 3 is an exploded view of a particulate matter sensor.

FIG. 3 is an exploded perspective view of the sensing element 140 of FIG. 2. The sensing element 140 includes an electrically insulating substrate 154. While shown as a single layer, it will be appreciated that substrate 154 may be formed by laminating together a plurality of layers. Conductive material disposed on one surface of substrate 154 is patterned to form conductors 146 and 148 and electrodes 142 and 144. Resistor material to form bias resistor 150 is deposited so as to form a resistive path between conductors 146 and 148. A first protective layer 164 may also be included to protect the conductive material that forms electrodes 142 and 144, as well as portions of the conductors 146, 148 that may be exposed to abrasive particles in the gas stream being measured. The first protective layer 164 includes an open area 166 exposing the gap between the electrodes 142 and 144 to allow particulate matter to bridge the electrodes 142 and 144. The first protective layer 164 may also extend to cover bias resistor 150.

A particulate matter sensor may also include a heating means 160 that is controllable to raise the temperature in the vicinity of the electrodes 142, 144 on the sensing element. Raising the temperature sufficiently for a sufficient duration of time will result in particulate matter being removed from the surface of the sensing element, thereby restoring the resistance of the area between the sensing electrodes 142, 144 to a high resistance or essentially open circuit condition. This open circuit condition appears electrically in parallel with the bias resistor 150, so that the total resistance measured between connection means 37 and connection means 38 is restored to $R_{bias}$. The sensing element 140 depicted in FIG. 3 includes a heater 160 and heater leads 162, on the opposite surface of the substrate 154 from the electrodes 142, 144. The heater 160 is positioned to allow the heater 160 to clean the particulate matter from the vicinity of the electrodes 142, 144 when the heater 160 is electrically powered by supplying current through heater leads 162. A second protective layer (not shown) may be provided so as to encapsulate the heater 160 between the second protective layer and the substrate 154.

The heater 160 is provided to increase the temperature of the soot sensing element to be within a desired temperature range. In particular, the heater 160 generates heat in response to a signal received from the ECM 202. In one exemplary embodiment, the heater 160 can also periodically increase the temperature of the soot sensor 140 to at least 550 degrees Celsius to burn off the collected soot on the soot sensor 140. The heater 160 can also be energized to a higher temperature to burn off other contaminants that may be present on the soot sensor, as disclosed in commonly owned U.S. Patent Application Publication No. 2013/0000678 titled "METHOD AND SYSTEM FOR CONTAMINATION REMOVAL FROM A PARTICULATE MATTER SENSOR", the contents of which are herein incorporated by reference in their entirety. The aforementioned temperatures are merely provided as examples, and exemplary embodiments of the present invention are not intended to be limited to the specific temperature ranges provided herein.

Figure 4:
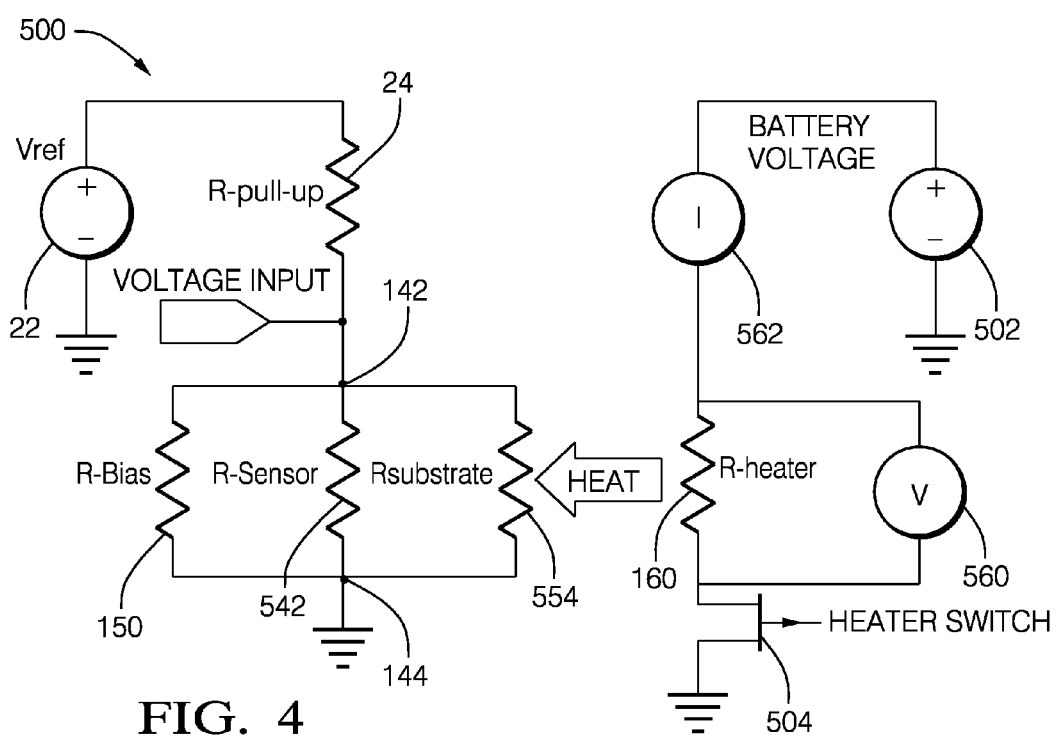
FIG. 4 is an electrical schematic of a portion of a particulate matter sensor system.

Referring now to FIG. 4, a non-limiting example of a particulate sensor system 500 is illustrated. The system includes a reference voltage source 22, a pull-up resistor 24, a bias resistor 150, and an arrangement for measuring the voltage across electrodes 142, 144. As shown in FIG. 4, voltage across the electrodes 142, 144 is dependent on the resistance between these electrodes. This resistance can be viewed as the parallel combination of three resistances, identified in FIG. 5 as 150, 542, and 554. Resistance 150 is the bias resistor, resistance 542 represents the resistance of material deposited between the sensing electrodes 142 and 144, and resistance 554 represents the resistance contribution of the material that comprises substrate 154 in FIG. 3, as measured between electrodes 142 and 144. The substrate typically has a high resistivity such that resistance 554 can for most purposes be ignored, that is, treated as an open circuit.

FIG. 4 also includes a voltage source 502 configured to deliver energy to the heater 160 when a heater switch 504 is turned on in response to a control signal commanding the heater to turn on. The heater may be provided with a pulse width modulated (PWM) heater drive voltage, for example with full battery voltage applied to the heater for an "on time" period, and essentially zero volts applied to the heater for an "off time" period. The duty cycle, defined as (on_time)/(on_time+off_time), can be controlled to achieve the desired sensor temperature. The "effective" heater voltage is approximately equal to the full battery voltage times the duty cycle percentage.

It will be appreciated from the foregoing description that the effective resistance measured between the electrodes 142, 144 is a function of the amount and the conductivity of the material deposited on the surface of the sensor in the gap between the electrodes 142, 144. In normal engine operation this material will be soot. However, under certain conditions other materials such as a contaminant comprising material from an additive in the engine fuel or lubricating oil may be deposited on the soot sensor. The presence of a contaminant may impair the ability of the sensor to perform its intended function, namely to indicate soot in the exhaust gas.

Additionally, it is desirable to recognize an attempt to tamper with the soot sensing system by replacing the soot sensor with a fixed resistor having a resistance value that is within the range of resistance that would pass a "rationality" test, that is, a resistance that would correspond to an expected resistance value that might be read from a properly operating soot sensing system.

To address the need for diagnostics for a soot sensing system, the method of the current invention has been developed. In an aspect of this method, the relationship between resistance and temperature for a particulate matter sensor with a fixed amount of soot loading is determined. It has been observed that soot has a resistance vs. temperature characteristic such that the electrical resistance decreases as the temperature increases (negative temperature coefficient, or NTC characteristic). With a given constant amount of soot collected on the sensor element, the electrical resistance measured across the sensor element should depend only on the temperature of the sensor element.

Figure 5:
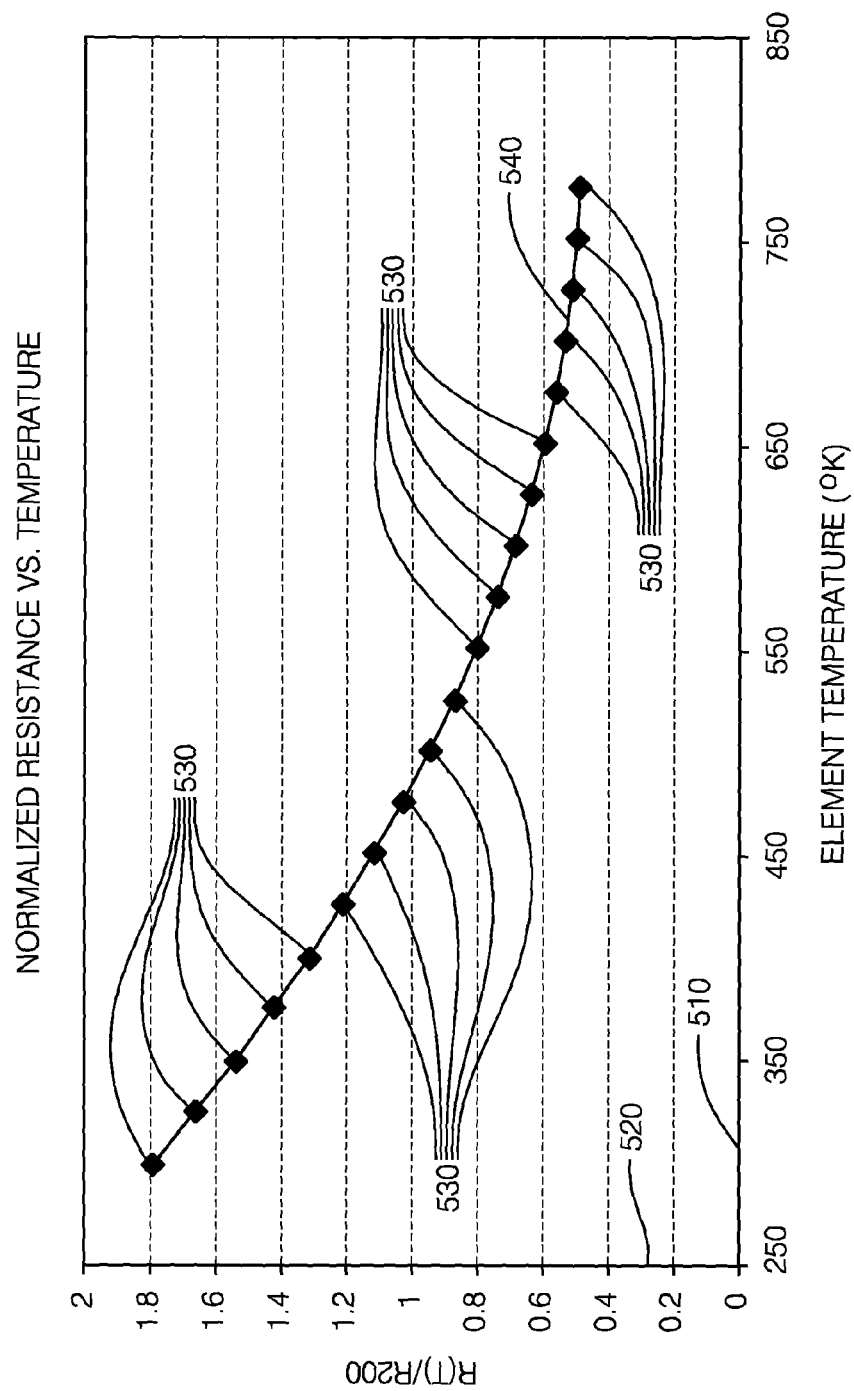
FIG. 5 is a depiction of an exemplary normalized resistance vs. temperature characteristic of soot on a particulate matter sensor.

FIG. 5 is a depiction of an exemplary normalized resistance vs. temperature characteristic of soot on a particulate matter sensor. To obtain the plot presented in FIG. 5, the resistance of a soot sensor with a given amount of soot deposited thereon was measured at a number of temperatures. Each resistance was then normalized by dividing the measured resistance at a given temperature by R200, the resistance measured at a reference temperature, in this case 200° C. (473 K). In FIG. 5, each point 530 represents a normalized resistance value R(T)/R200, with the x-axis 510 representing sensing element temperature (Kelvin) and the y-axis representing the magnitude of the normalized resistance R(T)/R200.

Using curve fitting, the normalized resistance vs. temperature behavior of a loaded soot sensor can be represented by a mathematical function. In the example given in FIG. 5, the normalized resistance vs. temperature of a loaded soot sensor was found to have a good fit over a temperature range of 100° C. to 450° C. with a second order polynomial function of temperature, given as $$y(T) = \frac{R(T)}{R200}$$
$$= aT^2 + bT + c$$

where T=Temperature
R(T)=Sensor resistance at temperature T
R200=Sensor resistance at 200° C.
a=5.42×10$^{-6}$
b=−8.56×10$^{-3}$
c=3.87

The solid line 540 in FIG. 5 represents this equation y(T)=5.42·10$^{-6}$ T$^2$−8.56·10$^{-3}$ T+3.87. It will be noted that, as expected, the normalized resistance 530, 540 in FIG. 5 has a value of unity at a temperature of 200° C. (473 K).

The forgoing equation and coefficients listed for y(T) provide a non-limiting example to illustrate an aspect of the invention. While a second order polynomial equation is illustrated, it will be appreciated that a different mathematical function or a lookup table may alternatively be used to represent the expected relationship between normalized resistance and temperature. Also, it will be appreciated that the selection of 200° C. is somewhat arbitrary in that any temperature within the temperature range of interest may be chosen for normalizing. Further, it will be appreciated that the actual numerical values of the coefficients may be influenced by other factors, for example by the temperature coefficient of resistance (TCR) of the bias resistor 150 and by the resistance of the bias resistor 150 relative to the resistance of the soot collected on the sensor.

Figure 6:
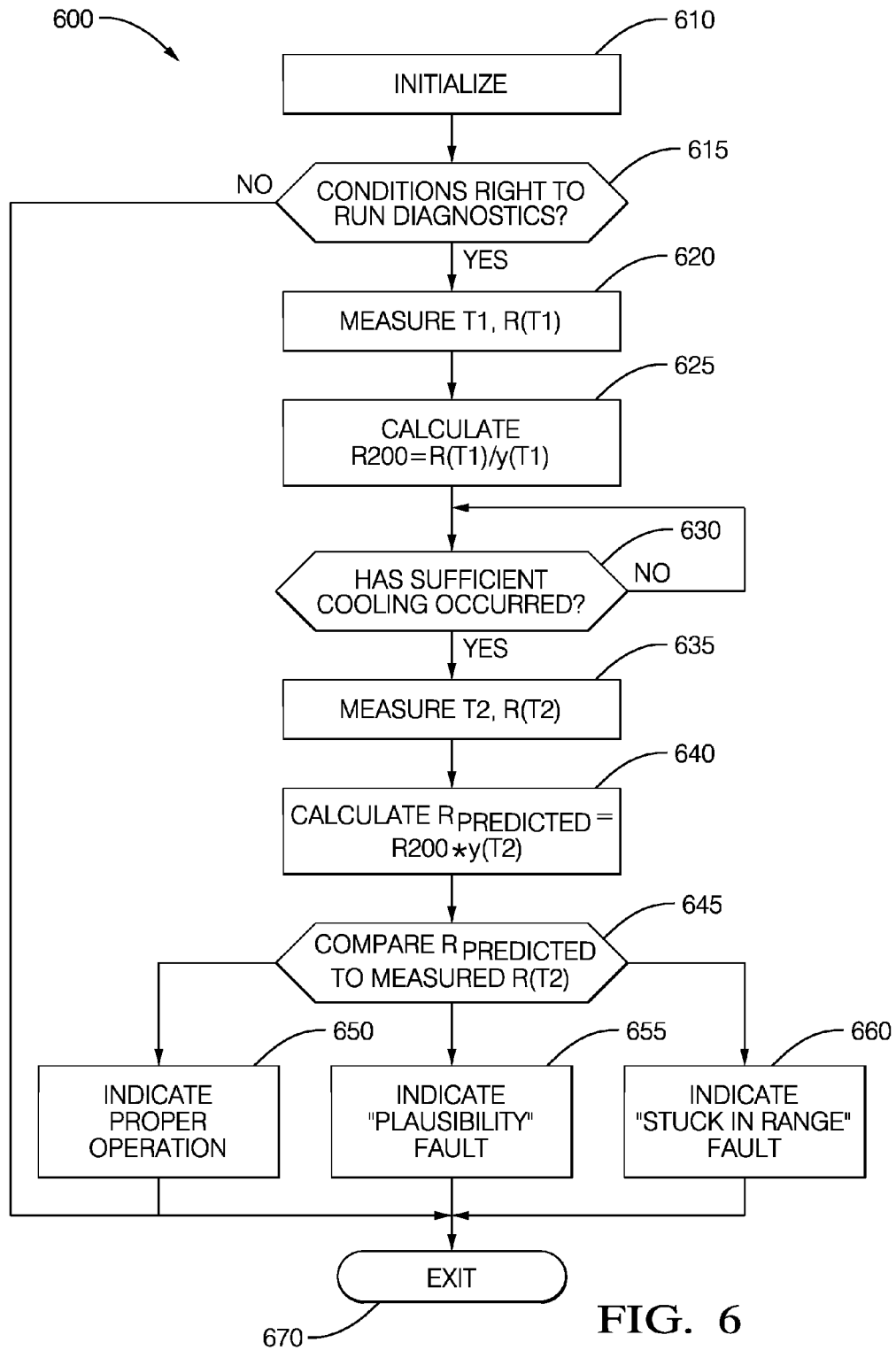
FIG. 6 is a flow chart of a method incorporating aspects of the present invention.

FIG. 6 is a flowchart illustrating steps of a non-limiting method 600 that incorporates aspects of the present invention. After performing any necessary initialization in step 610, the method proceeds to step 615, where it is determined if conditions are proper for initiating a cool-down diagnostic test. If it is determined that conditions are not proper for initiating the cool-down diagnostic test, the method exits at step 670.

In order to use the temperature dependence of normalized resistance as a basis for diagnostics it is necessary to ascertain that any variation in measured resistance over the course of the diagnostic test is the result of temperature change and is not caused by a change in the amount of accumulated soot on the sensor surface over the course of the test. Accordingly, in an aspect of the present invention, the diagnostic test in performed during engine operating conditions where additional soot is not being presented to the sensor. One such operating condition is known as deceleration fuel cut-off (DFCO). DFCO is an engine control strategy in which injection of fuel to the engine is ceased when the driver input calls for the vehicle to decelerate. DFCO can result in fuel saving, as well as using engine braking to reduce wear on the vehicle friction brake components. Because no fuel is injected during DFCO, combustion does not take place. As a result, no additional soot is generated and exhaust temperature decreases during DFCO.

Another engine operating condition that may be used to initiate the diagnostic method of the present invention is engine stop. Like DFCO, the time immediately following stopping an engine is characterized by no additional soot generation and by decreasing exhaust temperature.

In addition to engine operating condition, other factors that may be used in determining in step 615 the appropriateness of performing the diagnostic test include the exhaust temperature and the resistance measured across the electrodes of the sensor. By way of non-limiting example, it may be desirable to perform the diagnostic test only when the exhaust temperature is above 100° C. in order to ensure that there is no liquid water condensate on the surface of the sensor. It may be desirable to only initiate the diagnostic test when the exhaust temperature is below a maximum temperature threshold so as to be within a temperature range where the behavior of y(T), the normalized resistance ratio, is well characterized. Other factors that may be used in step 615 to determine whether to initiate the diagnostic test include engine run time and/or time spent in DFCO. When it has been determined in step 615 that the diagnostic test should be initiated, the exhaust temperature T1 and the sensor resistance R(T1) are measured in step 620. The method then proceeds to step 625, where the value R200, an estimate of what the soot resistance would be at 200° C., is determined. Using the example presented earlier where the relationship between normalized resistance and temperature may be expressed as a polynomial, namely:

$$y(T) = \frac{R(T)}{R200}$$
$$= aT^2 + bT + c$$

the value of R200 can be determined from the predetermined coefficients a, b, c, the measured resistance R(T1), and the measured temperature T1 as:

$$R200 = \frac{R(T1)}{y(T1)}$$
$$= \frac{R(T1)}{a(T1)^2 + b(T1) + c}$$

With continued reference to FIG. 6, following the determination of R200 in step 625 the method proceeds to step 630, where the method waits for sufficient cooling of the sensor to take place before proceeding further. The wait interval may be based on elapsed time, exhaust temperature determination, or a combination thereof.

Following the determination in step 630 that sufficient cooling of the sensor has occurred, the method 600 proceeds to step 635 where the exhaust temperature T2 and the sensor resistance R(T2) are captured, and the method proceeds to step 640.

In step 640, a predicted value for the resistance at the temperature T2 is calculated. Again rearranging the equation relating normalized resistance to temperature, namely:

$$y(T) = \frac{R(T)}{R200}$$
$$= aT^2 + bT + c$$

a predicted resistance at the temperature T2 can be determined from the predetermined coefficients a, b, c, the measured temperature T2, and the value of R200 determined in step 625 as:

$$Rpredicted = R200 \times y(T2)$$
$$= R200 \times (a(T2)^2 + b(T2) + c)$$

The method 600 then proceeds to step 645.

It has been observed that the normalized resistance vs. temperature behavior of a sensor with soot deposited thereon differs from a normalized resistance vs. temperature characteristic of a sensor having contaminants other than soot deposited thereon. This observation provides the basis for a diagnostic method for a soot sensor that incorporates aspects of the present invention. In step 645 Rpredicted, the predicted resistance value at T2 calculated in step 640, is compared with the measured resistance R(T2) that was determined in step 635.

If it is determined in step 645 that the difference between the predicted value Rpredicted and the measured resistance R(T2) is within a predetermined range, the method proceeds to step 650, where proper operation of the soot sensor is indicated. As used herein, the phrase "difference between the predicted value and the measured resistance" is not limited to the common mathematical definition of difference meaning the result of a subtraction operation. The difference may be evaluated in other ways that indicate lack of agreement between the predicted and measured values, for example by evaluating a ratio of the predicted and measured values. After indicating proper sensor operation in step 650, the method then exits at step 670.

If it is determined in step 645 that the predicted value Rpredicted does not agree with the measured resistance R(T2) within the threshold that would indicate proper operation, a comparison may be made between the measured value R(T1) from step 620 and the measured value R(T2) from step 635. This comparison may be based on, for example, subtracting the measured resistances from each other or by calculating a ratio of the measured resistances. If this comparison indicates that R(T1) and R(T2) are sufficiently close to each other, the method proceeds to step 660, where a "stuck in range" fault is indicated. This condition may exist, for example, if a particulate sensor system is tampered with by replacing the soot sensor 140 with a fixed resistor. After indicating a "stuck in range" fault in step 660, the method then exits at step 670.

If the comparison in step 645 determines that neither proper sensor operation nor a "stuck in range" fault exists, the method proceeds to step 655 where a plausibility fault is indicated. After indicating a plausibility fault in step 655, the method then exits at step 670.

In the foregoing description, steps 650, 655, and 660 are described as "indicating" a condition, either proper operation or a fault condition. As non-limiting examples, the "indicating" step may comprise setting a flag in a controller memory location, generating a diagnostic code to be read by a diagnostic scanner, or turning on a malfunction indicator lamp.

While this invention has been described in terms of embodiments thereof, it is not intended to be so limited, but rather only to the extent set forth in the claims that follow.

The invention claimed is:

1. A method for diagnosing a particulate matter sensing system, said system comprising an electronic controller portion, an electrical connection means connected to the controller portion, and a sensing element connected to the electrical connection means, said sensing element comprising two electrodes spaced from one another, said method comprising the steps of:
   determining at a first time during a cool-down event a first sensing element temperature and a resistance of the sensing element;
   determining at a second time during the cool-down event a second sensing element temperature and the resistance of the sensing element, the second time occurring later than the first time;
   calculating in the electronic controller portion a predicted sensing element resistance at the second sensing element temperature, wherein the predicted sensing element resistance is based on the first sensing element temperature, the resistance of the sensing element determined at the first time, and a predetermined model of a resistance vs. temperature characteristics of the sensing element;
   comparing the predicted sensing element resistance at the second sensing element temperature to the resistance of the sensing element determined at the second time; and
   indicating a fault condition if a difference between the predicted sensing element resistance at the second sensing element temperature and the resistance of the sensing element determined at the second time is not within a predetermined range.

2. A method according to claim 1, wherein the cool-down event is a deceleration fuel cut-off (DFCO) event.

3. A method according to claim 2, wherein the first time is the beginning of the DFCO event and the second time is the end of the DFCO event.

4. A method according to claim 1, wherein the cool-down event is an engine stop event.

5. A method according to claim 4, wherein the first time is the time at which the engine is stopped and the second time is the time at which the engine is restarted.

6. A method according to claim 1, further comprising determining the temperature of the sensing element, and wherein the method steps of claim 1 are only performed when the temperature of the sensing element is within a predetermined range.

7. A method according to claim 1, wherein the predetermined model of the resistance vs. temperature characteristics is a model of a normalized resistance vs. temperature, wherein the normalized resistance is a ratio of resistance at a temperature and resistance at a reference temperature.

8. A method according to claim 1, wherein the difference between the predicted sensing element resistance at the second sensing element temperature and the resistance of the sensing element determined at the second time is calculated as a ratio of the predicted sensing element resistance at the second sensing element temperature and the resistance of the sensing element determined at the second time.

9. A method according to claim 8 wherein proper operation of the particulate matter sensing system is indicated if the ratio is within a predetermined range.

10. A method according to claim 9 wherein proper operation of the particulate matter sensing system is indicated if the ratio is in a range of approximately 0.8 to 1.2.

11. A method according to claim 8 wherein a plausibility fault of the particulate matter sensing system is indicated if the ratio is not within a predetermined range and if the resistance of the sensing element determined at the second time differs from the resistance of the sensing element determined at the first time by more than a predetermined resistance change threshold.

12. A method according to claim 11 wherein the predetermined resistance change threshold is approximately 30 kilohms.

13. A method according to claim 11 wherein the predetermined range for the ratio is 0.8 to 1.2.

14. A method according to claim 1, wherein a difference between the resistance of the sensing element determined at the second time and the resistance of the sensing element determined at the first time is calculated by a subtraction between the resistance of the sensing element determined at the second time and the resistance of the sensing element determined at the first time.

15. A method according to claim 14, wherein a stuck in range fault is indicated if the resistance of the sensing element determined at the second time differs from the resistance of the sensing element determined at the first time by less than a predetermined resistance change threshold.

16. A method according to claim 15 wherein the predetermined resistance change threshold is approximately 30 kilohms.

17. An apparatus comprising a controller and a non-transitory computer readable medium containing instructions that, when executed, cause the controller to perform the method of claim 1.

* * * * *